(12) United States Patent
Nyholm

(10) Patent No.: US 8,620,462 B2
(45) Date of Patent: Dec. 31, 2013

(54) APPARATUS IN DENTAL ENVIRONMENT AND METHOD FOR CONTROLLING A DEVICE BELONGING TO THE SAME

(75) Inventor: Kustaa Nyholm, Siuntio (FI)

(73) Assignee: Planmeca Oy, Helsinki (FI)

( * ) Notice: Subject to any disclaimer, the term of this patent is extended or adjusted under 35 U.S.C. 154(b) by 940 days.

(21) Appl. No.: 12/084,585

(22) PCT Filed: Nov. 22, 2006

(86) PCT No.: PCT/FI2006/050510
§ 371 (c)(1),
(2), (4) Date: May 6, 2008

(87) PCT Pub. No.: WO2007/060292
PCT Pub. Date: May 31, 2007

(65) Prior Publication Data
US 2009/0162808 A1      Jun. 25, 2009

(30) Foreign Application Priority Data

Nov. 22, 2005   (FI) ..................................... 20051190

(51) Int. Cl.
*A61C 19/00* (2006.01)
(52) U.S. Cl.
USPC .............................................. 700/83; 433/25
(58) Field of Classification Search
USPC .................. 700/17, 83; 433/25, 215, 229; 340/539.11, 539.12, 539.13; 600/300, 600/301
See application file for complete search history.

(56) References Cited

U.S. PATENT DOCUMENTS 5,752,827 A * 5/1998 Baron et al. ..................... 433/68
5,854,624 A   12/1998 Grant (Continued)

FOREIGN PATENT DOCUMENTS

DE       19857613      12/1998
EP        1010404      12/1999

(Continued)

OTHER PUBLICATIONS

International Search Report of PCT/FI2006/050510 mailed Mar. 7, 2007.

(Continued)

*Primary Examiner* — Charles Kasenge
(74) *Attorney, Agent, or Firm* — Stites & Harbison PLLC; Juan Carlos A. Marquez, Esq.; Stephen J. Weyer

(57) ABSTRACT

The present invention relates to an apparatus used in dental care environment and to a method for controlling a device belonging to the apparatus, especially to hygienic and ergonomic control of a device belonging to the apparatus in connection with dental care work. The invention includes at least one device (2, 3) used in connection with dental care work, such as a dental unit, a patient chair, a dental x-ray device and/or a computer and at least one user interface (1) for sending control commands to at least one of said devices (2, 3) used in connection with dental care work, whereby a fixed or a detachable means (4) is arranged in said user interface (1) for detachably connecting it to a person working in the dental care environment, to his/her clothing or to the dental unit, or the user interface is arranged as a fixed or a detachable part of clothing arranged to be separately dressed on the person in question or of some other structure to be dressed on.

37 Claims, 5 Drawing Sheets

(56) References Cited

U.S. PATENT DOCUMENTS

Figure 1:
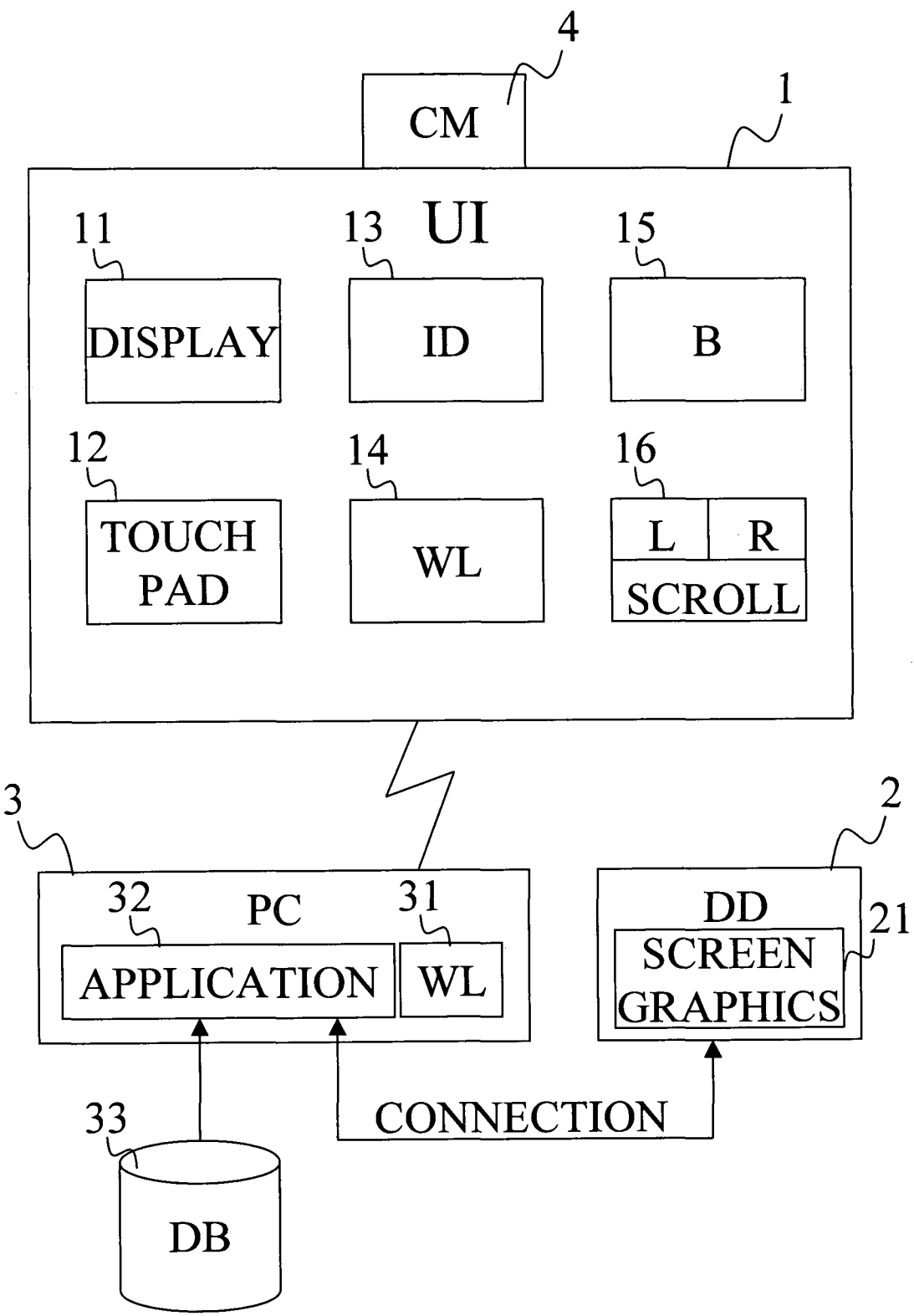

| | | | |
|---|---|---|---|
| 6,157,454 A * | 12/2000 | Wagner et al. | 356/407 |
| 6,182,169 B1 * | 1/2001 | Force et al. | 710/62 |
| 6,201,484 B1 | 3/2001 | Russell | |
| 6,288,704 B1 * | 9/2001 | Flack et al. | 345/158 |
| 6,358,202 B1 * | 3/2002 | Arent | 600/300 |
| 6,513,532 B2 * | 2/2003 | Mault et al. | 600/595 |
| 6,525,819 B1 * | 2/2003 | Delawter et al. | 433/29 |
| 6,754,069 B2 * | 6/2004 | Harada | 361/679.03 |
| 6,754,472 B1 * | 6/2004 | Williams et al. | 455/100 |
| 6,786,866 B2 * | 9/2004 | Odagiri et al. | 600/300 |
| 7,006,600 B1 * | 2/2006 | Krema et al. | 378/98.7 |
| 7,008,387 B2 * | 3/2006 | Saruwarati et al. | 600/595 |
| 7,296,752 B2 * | 11/2007 | Carnevali | 235/462.44 |
| 7,480,492 B2 * | 1/2009 | Williams et al. | 455/100 |
| 7,739,125 B2 * | 6/2010 | Sorensen et al. | 705/2 |
| 2003/0195644 A1 | 10/2003 | Borders et al. | |
| 2003/0208110 A1 * | 11/2003 | Mault et al. | 600/300 |
| 2004/0010599 A1 * | 1/2004 | Otobe | 709/228 |
| 2004/0057340 A1 * | 3/2004 | Charles-Erickson et al. | 368/10 |
| 2004/0114034 A1 * | 6/2004 | Squilla et al. | 348/66 |
| 2004/0152957 A1 * | 8/2004 | Stivoric et al. | 600/300 |
| 2004/0152961 A1 * | 8/2004 | Carlson et al. | 600/301 |
| 2005/0053199 A1 * | 3/2005 | Miles | 378/197 |
| 2005/0110640 A1 * | 5/2005 | Chung | 340/572.1 |
| 2005/0130097 A1 * | 6/2005 | Warner | 433/77 |
| 2005/0130098 A1 * | 6/2005 | Warner | 433/77 |
| 2005/0240086 A1 * | 10/2005 | Akay | 600/300 |
| 2006/0166720 A1 * | 7/2006 | Dixon | 455/575.6 |
| 2006/0195035 A1 * | 8/2006 | Sun | 600/503 |
| 2007/0085690 A1 * | 4/2007 | Tran | 340/573.1 |
| 2008/0146887 A1 * | 6/2008 | Rao et al. | 600/300 |

FOREIGN PATENT DOCUMENTS

| | | |
|---|---|---|
| JP | 06-154249 | 6/1994 |
| JP | 11-226035 | 8/1999 |
| JP | 2001-165968 | 6/2001 |
| WO | WO 2004/084753 | 3/2004 |
| WO | WO 2005016164 | 2/2005 |

OTHER PUBLICATIONS

Finnish Search Report of PCT/FI2006/050510 mailed Aug. 7, 2006.

* cited by examiner

APPARATUS IN DENTAL ENVIRONMENT AND METHOD FOR CONTROLLING A DEVICE BELONGING TO THE SAME

The invention relates to an apparatus used in dental care environment and to a method for controlling a device belonging to the apparatus, especially to hygienic and ergonomic control of a device belonging to the apparatus in connection with dental care work. The apparatus includes at least one device used in connection with dental care work, such as a dental unit, a patient chair, a dental x-ray device and/or a computer and at least one user interface for sending control commands to at least one of said devices used in connection with dental care work.

It is important to keep the dental care environment hygienic in order to ensure the safety of it. The purpose of disinfection is to guarantee that no microbes find their way from the devices including to the dental care environment and instruments used in the treatments either to the patients or the care staff. Suitable disinfection methods, depending on the object, are e.g. thermal sterilization by boiling or in an autoclave or chemical disinfection, such as wiping with suitable disinfectant or soaking in a disinfectant solution. When choosing a suitable method, attention has to be paid to the material to be treated, among other things, since e.g. a plastic surface may absorb disinfectant and many materials do not withstand high temperatures. Further, e.g. many instruments and other objects including e.g. sensitive electronics do not endure autoclaving.

As also elsewhere in society, use of computers has increased in the dental care environment, too. Also devices used in connection with dental care work increasingly contain functions the control of which is based on computer programs, as a result of which various user interfaces known in connection with computers have become more common also in the dental care environment. As not only sterility of the dental instruments but also regular disinfecting of the devices and other surfaces included in the dental care environment is essential in view of safety of the dental care environment, e.g. the traditional keyboard and mouse user interfaces are quite problematic in this respect. E.g. autoclaving of them is naturally totally impossible, just as well as embedding them in any disinfectant solution, and even wiping with disinfectant is problematic since both the mouse and the keyboard contain, among other things, irregular surfaces and narrow gaps between their various moving parts.

Although computerization, digitalisation of devices, increase in the use of software applications included in them and their development bring along many advantages, many times they also create new problems. One such a problem relates to how these possibilities brought along by the new technology could be taken advantage of as simply and ergonomically as possible in connection with operations performed in the dental care environment. E.g. when performing care operations, the dental staff typically works in a work station located in the immediate vicinity of a patient chair and the operations typically require touching e.g. mucous membranes of the patient. In case in connection with this a need arises to use such a device used in the dental care environment the user interface of which is not located in the immediate vicinity of the care work station, the care work needs to be interrupted and one will have to move at the user interface of the device in question at the time. E.g. a computer with its user interface is typically located on a table of its own, possibly at a distance from the care work station, so that the person attending dental care is forced to move from one work station to another in order to be able use the computer in connection with the dental care operation. The computer is typically controlled by a keyboard and a mouse, the hygienic use of which e.g. through disposable protective bags and/or keeping them hygienic includes problems of its own. On the other hand, if it is not possible to arrange use of the user interface reliably hygienic, a hygiene risk is caused in addition to interruption of the care work, when after use of the user interface one should return to continue with the dental care operation.

The prior art also includes use of e.g. various touch pads, touch screens or push buttons to be used through a solid membrane or integrated in a membrane as user interfaces for dental units, dental x-ray devices and computers, for example. A far as they are concerned, taking care of hygiene is of a degree easier when compared to the keyboard and the mouse, but in view of ergonomics of the dental care work, the situation is still far from ideal in case the user interface is located at a different work station than the one where the dental care is being attended, anyway. This being the case, it will not be possible to scan and process patient information, such as an electric patient card, from the care work station, to add information thereto or e.g. see from the screen or present on the screen to the patient photographs and/or x-ray images taken of the denture. During dental care work, naturally, treatment instruments controlled via dental unit are often used whereby, depending on the functions and/or the control possibilities offered by the dental unit, the actual work being associated with the dental care work may have to be interrupted and/or the working position to be broken up and found again after having given a control command.

Among other things, because of the abovementioned ergonomic reasons, for example, more suitable places for placing user interfaces of the devices than the traditional ones have thus been searched for. An idea has been presented, among other things, to integrate the user interface in a suitable place of the patient chair from the point of view of the dental care work, and even dental units to be controlled by speech have been designed. The object of the present invention is, however, to reach a solution based on more traditional user interface techniques than the speech control, which still enables a hygienic and flexible solution for controlling devices used in the dental care environment and, specifically in preferable embodiments in view of the dental care work itself, also an ergonomic solution.

The object of the invention is reached by the invention according to the following independent claims, preferable embodiments of which have been specified in following dependent claims. Means arranged in the user interface for detachably connecting it to a person working in the dental care environment, to his/her clothing or to the dental unit form an essential part of the invention, or the user interface has been arranged as a fixed or a detachable part of clothing or other structure arranged to be separately dressed on the person in question. When the user interface is arranged to be attached to a wrist or a forearm, for example, depending on the embodiment of the invention, a dentist may give a desired control command either to a certain device or a device desired by him/her being located in the dental care environment without actually changing his/her working position hardly at all even if he/she were simultaneously operating in the patient's mouth, in a position reaching over the patient.

By arranging, on one hand, the user interfaces according to the invention to contain an individual identification code and, on the other hand, even more than one device used in the dental care environment to recognize such a code, such an embodiment of the invention may be realized in which each person attending the dental care work has his/her own personal portable user interface, by which same user interface one may then control, depending on the embodiment of the invention, e.g. several dental units, x-ray devices and/or computers being located in the dental care environment in question. If desired, such an embodiment may be implemented in such a way that knowledge of who at the given time has given the control commands in question becomes at the same time automatically stored in the user log of a device used or e.g. to a patient card. Further, rights of different levels being based on the identification code may be arranged to the devices included in this kind of apparatus, e.g. in such a way that the device is arranged to accept as control commands only signals including such an identification code it recognizes and/or that some of the functions of the device require user rights of higher level than some other of its functions. Naturally, based on the same principle, use of a device may be completely prevented from others than those user interfaces, which are capable of sending such an identification code the device recognizes.

Figure 2:
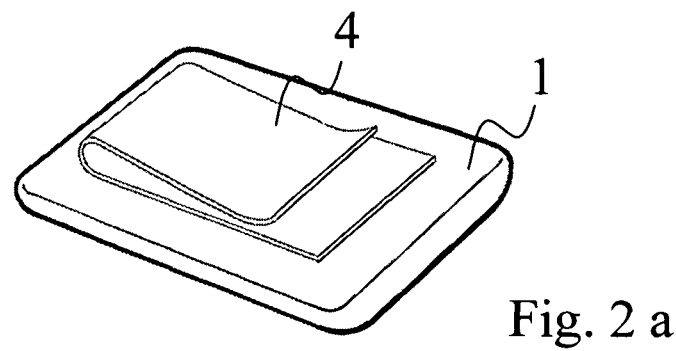
Figure 2:
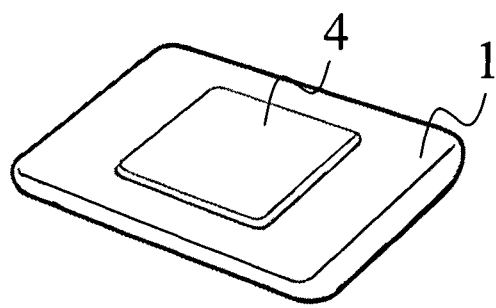
Figure 2:
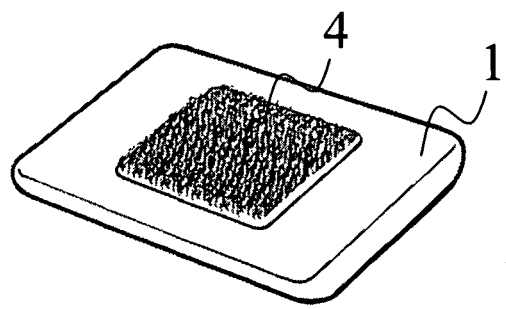
Figure 2:
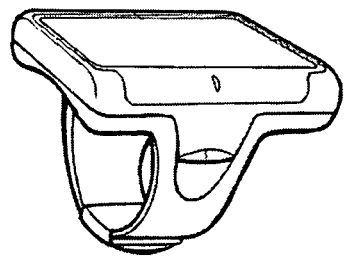
Figure 2:
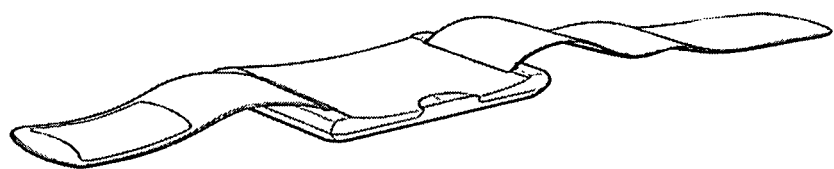
Figure 3:
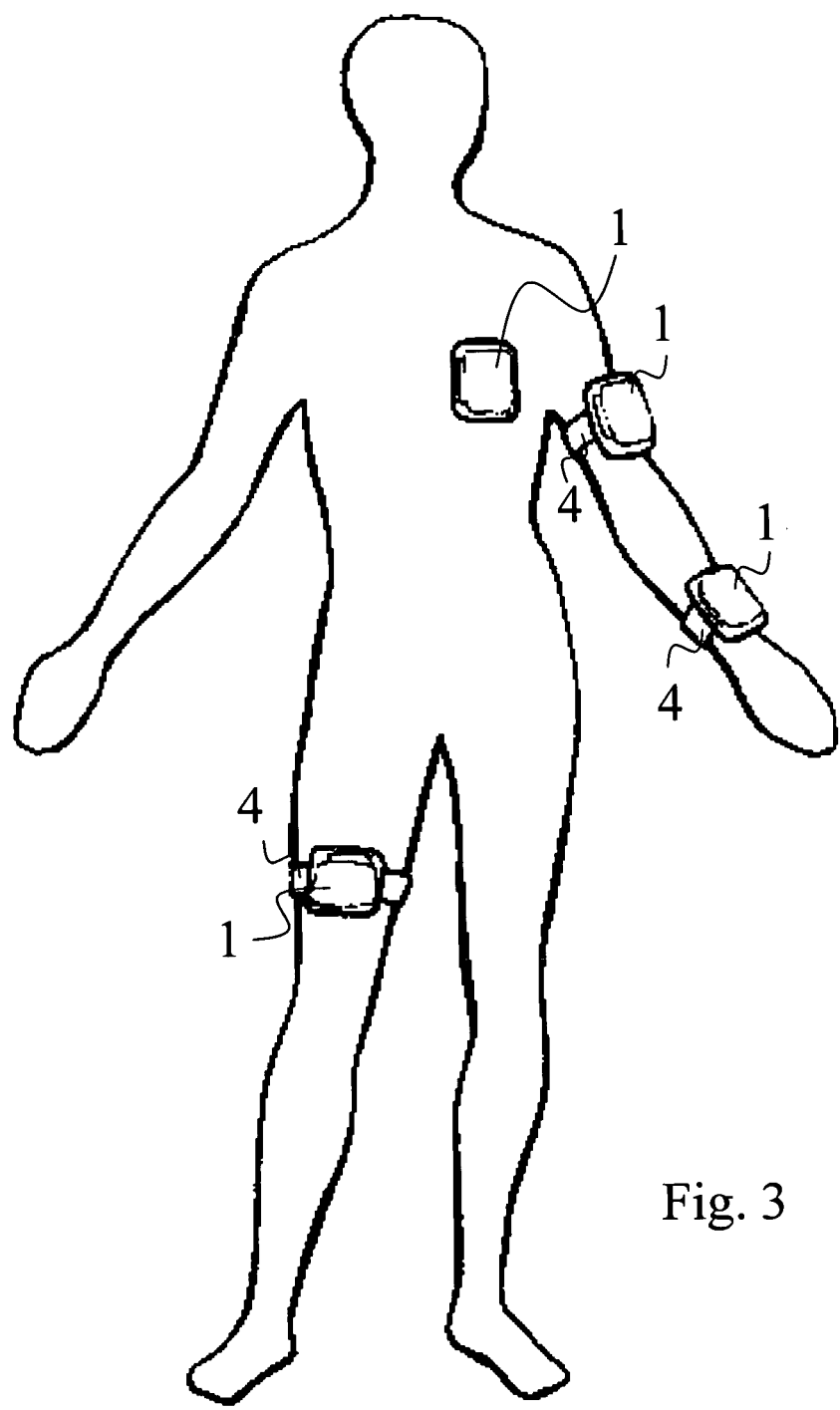
Figure 4:
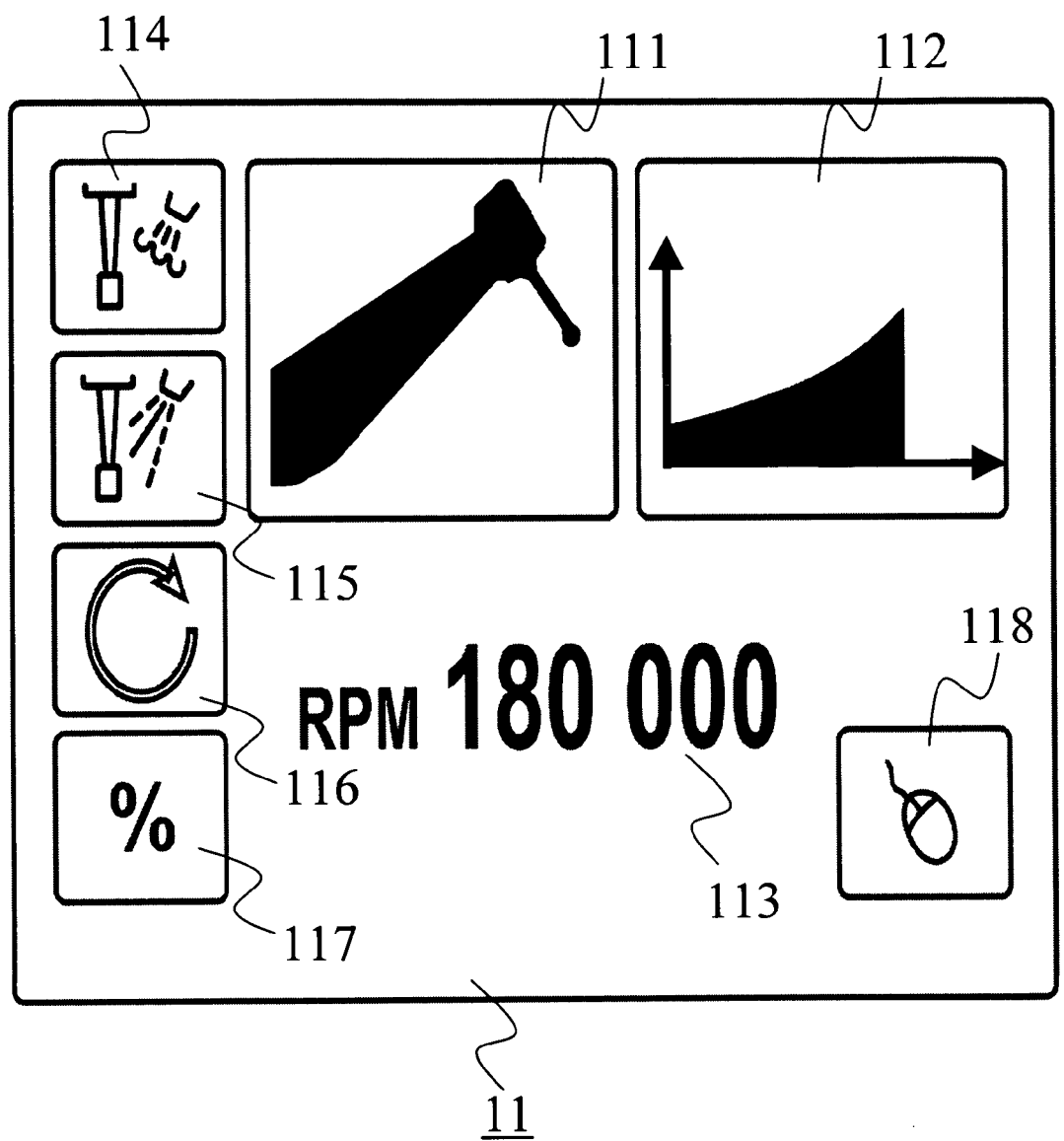

This kind and other preferable embodiments of the invention, together with other advantages reachable by various embodiments of the invention are presented in more detail in the following by also referring to the following figures, of which FIG. 1 presents a block diagram of a structure and operation principle of one preferable embodiment of the apparatus according to the invention for controlling operation of a device included in the dental care environment by an user interface according to the invention, FIGS. 2a-2e present some solutions according to preferable embodiments of the invention for connecting means of the user interface according to the invention, FIG. 3 presents preferable embodiments of the invention for detachably connecting a user interface to the person working in the dental care environment and FIG. 4 presents a function key/screen layout of a surface of a user interface according to one preferable embodiment of the invention.

FIG. 1 presents as a block diagram the structure and the operation principle of one preferable embodiment of the apparatus according to the invention for controlling operation of a device included in the dental care environment by a user interface according to the invention. The apparatus according to FIG. 1 includes a user interface UI (1) including connecting means CM (4) and a device belonging to the dental care environment DD (2). In the apparatus, the device belonging to the dental care environment (2) is e.g. a dental unit, which is connected to the same network with another device also belonging to the dental care environment, in the case according to FIG. 1, with a computer PC (3). The user interface (1) according to FIG. 1 contains a DISPLAY (11), a TOUCH PAD (12), a memory circuit containing an identification code ID (13), a transmitter or a transmitter-receiver of a wireless link WL (14), a battery B (15) and a push button arrangement (16) enabling control functions corresponding the so-called left/right click L/R and SCROLL functions of a traditional mouse.

In the solution according to FIG. 1, in a computer (3) a wireless transmitter or transmitter-receiver WL (31) has been arranged in functional connection with a wireless (transmitter or transmitter-receiver 14) of the user interface (1). The link (14, 31) thus formed is preferably based on e.g. Bluetooth or WirelessUSB technology and is preferably arranged to enable directional data transfer, but the data transmission may also be, in principle, unidirectional (e.g. IR) or wired. In the apparatus according to FIG. 1, the computer (3) has been arranged to search for computer program APPLICATIONs (32) which have been stored in the database DB (33), which applications (32) may be associated with e.g. functions of the dental unit, the patient chair or the dental x-ray device (2). The software may also be some other software to be used in connection with the dental care environment. The graphics SCREEN GRAPHICS (21) produced in the device (2) used in connection with the dental care work in question may also be transmitted via the network (4) and the transmission link (31, 14) to the display (11) arranged in connection with the user interface (1).

When using wireless data transmission, it is preferable to arrange the apparatus to enable also a wireless power transmission to the user interface (1), which together with the wireless data transmission enables implementing the user interface (1) as hermetically tight and of such material that e.g. its cold sterilization not only by wiping but also by embedding to a liquid, or even autoclaving or other thermal sterilization, will be possible. To enable wireless data transmission, the link (14) of the user interface (1) may be arranged to also contain e.g. an inductive receiver, which is arranged to supply energy received from some external inductive transmitter to a battery (15) or to some other component capable of storing energy arranged in the user interface (1). In some embodiment, the wireless data transmission may even be thought to be arranged to take place continuously or "ON DEMAND", in which case the battery (15) or equivalent is not needed at all. The wireless transmitter or the transmitter/receiver (14) used in the data transmission arranged in the user interface may contain an inductive transmitter/receiver and/or a radio antenna (RFtransmitter/receiver). On the other hand, from the point of view of sterilizability, such a detachably connectable means may be arranged to the user interface (1), which is disposable or sterilizable by heat and via or through which control commands may be given from the user interface (1).

According to one preferable embodiment of the invention, the device (2, 3) used in connection with dental care work has thus been arranged in functional connection with the display (11). However, the display (11) does not necessarily have to lie in connection with the user interface (1), but it may also be some other display (11) functionally connected to the device (2, 3) used in connection with dental care work. When the device used in connection with dental care work is a computer (2), for example, it may be a display functionally connected to a computer. The display used in the apparatus may be e.g. a liquid crystal display, an organic LED-display or a so-called electronic ink/paper display. The apparatus may for sure include even more displays, such as e.g. a display arranged in the user interface and a display arranged in connection with the computer and/or the dental unit.

Preferable embodiments according to the invention, of the means for detachably connecting the user interface (1) to a person working in the dental care environment, to his/her clothing or to the dental unit, have been presented in FIGS. 2a-2e. The connecting means (4) of the user interface (1) according to FIG. 2a contains a clip by which the user interface is detachably connectable to e.g. a belt included in the clothing, or to an edge of a pocket. In the embodiment according to FIG. 2d, an adhesive tape (4) has been arranged to the user interface (1) by which it may be attached to e.g. the wrist, to the upper or the forearm or to the thigh. Naturally, there may be more adhesive tapes than one. As to FIG. 2b, the embodiment according to it contains a magnetic connecting piece (4), the embodiment according to FIG. 2c a connecting piece (4) containing adhesive surface and the embodiment according to FIG. 2e a ring-shaped connecting piece (4).

In FIG. 3 one presents how e.g. the embodiments according to FIGS. 2a and 2c enable detachable connection of the user interface (1) to a person's chest and e.g. the embodiments according to FIGS. 2d and 2e, e.g. to a person's upper arm, to a forearm/a wrist or to a thigh. The magnetic connecting means (4) according to FIG. 2b may be utilized for attaching the user interface (1) to a suitable location of a dental unit, for example. The means for detachably connecting the user interface (1) may also consist of more than one connecting means (4), e.g. of two parts being detachable from each other. The user interface (1) may also be implemented in such a way that several different means (4), which enable detachable connection, may be used in it, as e.g. solutions based on both adhesive and magnetic connection.

One preferable embodiment of the user interface (1) comprises including the electronics of the user interface in a housing, the lower surface of which having been arranged as curved. Compared to a flat surface, such a shape enables a more secure detachable connection e.g. to the wrist or to the thigh. Additionally, means such as a gravitational detector for recognizing the physical position of the user interface (1) may be arranged to it, and the operation of it may be arranged to become adjusted according to its physical orientation. If the user interface contains a touch pad, for example, it may be more natural for the user that the user interface interprets an up-down movement with respect to the direction of influence of gravitation to be a movement in the direction of the x-axis of an x-y coordinate system, whereas in some other orientation, it may feel more natural to interpret the corresponding movement on the surface of a touch pad to be a movement in the direction of the y-axis. Further, the corresponding change in the functionality of the user interface (1) can be arranged to be based on which kind of a connecting means (4) has been attached to the user interface (1). E.g. the connecting means (4) arranged for thigh attachment may be arranged to set the mode of operation of the user interface (1) different in this respect from the connecting means (4) intended for wrist attachment.

A contact surface of the user interface (1) may be arranged to contain control keys integrated under or on the surface of it and equipped with symbols. Especially when considering controlling of a dental unit, it is preferable, however, to arrange the user interface (1) to function as a touch screen in such a way that the view on the display (11) and also the control commands given via the user interface (1) are always changed based on which instrument of the dental unit, for example, is identified having been taken in use at a given time, in a way known as such. Hereby the symbols presented on the display (11) and control effect of them, i.e. in fact the operation mode of the user interface (1), are always changed on the instrument-by-instrument basis. A symbol of e.g. the dental instrument which has been identified having been taken in use, in a way known as such, as well as the operating power or rotation speed of the instrument as function of the time the instrument has been in use, or e.g. information of the status of the dental unit, can be shown on the screen (11). Also real time values of the operation parameters of the instruments or e.g. the limit value of the operation parameter in question may be presented. A symbol of a micromotor handpiece (111), the rotation speed of the micromotor instrument as a function of time of use and its momentary or the maximum rotation speed (113) possibly defined for it have been presented in the view of the display (11) according to FIG. 4. Additionally, for control functions of the instrument in question, symbols spray on/off (114) and chip blow on/off (115), a symbol for changing direction of rotation of the instrument (116) and a symbol for power limitation function on/off (117) have been presented on the display (11). Functionalities for choosing e.g. some other instrument and rotation speed range may be arranged in connection with the handpiece symbol (111) and the rotation speed display (112), too.

A view of the display (11) of the user interface (1) according to FIG. 4 also contains a push button or equivalent containing a symbol for change of the operation mode (118) of the user interface, with the help of which the operation mode of the user interface (1) may be between controlling of the dental unit and of the computer. According to the invention, the user interface (1) may contain even more corresponding actuators for changing its operation mode between controlling of other devices used in the dental care environment, such as a patient chair, various dental x-ray devices or a computer as well, or such a functionality may have been arranged in connection with a symbol (118) of one and the same user interface (1). As to x-ray devices, the view is preferably arranged to contain squares and control symbols (111-117) presenting functions and operation parameters of the device in a way corresponding to that shown in FIG. 4. The user interface (1) may be arranged to operate in the computer mode as a touch pad only, whereby by touching and moving on the surface of the touch pad, the cursor shown on a display (11) included in the apparatus, which may be the display of the device (2, 3) itself, may be controlled. On the other hand, corresponding graphics to that being presented on some other display (11) included in the apparatus may be presented on a display (11) arranged to the user interface (1), or arrange the graphics in question to be presented on the possibly only display of the apparatus only, arranged in connection with the user interface (1). In the latter case, the cursor is thus arranged to follow the touch and the movement on the touch pad directly on the screen (11) of the user interface (1).

An apparatus according to one preferable embodiment of the invention comprises a computer even if the user interface (1) was not arranged to control the computer in question but only some other device or devices (2, 3) included in the dental care environment. In such a case, namely, control commands given from the user interface (1) and/or values of the operation parameters when using the device (2, 3) in question may still be arranged to become automatically stored not only in the log file of the device (2, 3) possibly arranged thereto but also, or instead of it, in a database of a computer (33), such as in the log file concerning the device (2, 3) in question and/or in an electric patient information file.

For each of the users of the device or devices of the apparatus a user interface of their own may be arranged having an identification code individualizing the user interface (1), or means may be arranged in the user interface for receiving an identification code included in an identification signal sent by a transmitter, an identification card or equivalent carried along by each user, and means for sending this code e.g. as a part of each control signal to be sent from the user interface. Thereby, also the identification code individualizing the user of the device (2, 3) may be arranged to be automatically stored in the data file of history of use of the device (33) and/or e.g. in the patient file.

Also the user interface (1) in itself may be arranged to contain such a memory and data transmission means that the information of use and users described above can be automatically stored in the memory of the user interface, from where it can be transferred e.g. to the database of a computer (33) in conclusion of an individual operation, a patient visit or e.g. a working day. Such a memory may also be arranged e.g. in a separate user-specific identification/memory card, which is arranged to be connected to the user interface (1) or it is arranged in a wireless data transmission connection with the user interface (1).

The user interface (1) may be arranged in functional connection with more than one device (2, 3) included in the apparatus in such a way that each of the devices is arranged to send an identification signal of the same intensity individualizing itself and the operation mode of the user interface is arranged to set ready for controlling that device the identification signal from which is the strongest. Also means may be arranged to the user interface (1) for locking the operation mode to the desired, such as to the operation mode of the device sending the strongest identification signal. A corresponding functionality may be arranged by e.g. the GPS locating technique as well. Likewise, several identical or different user interfaces (1) according to the invention may be arranged for controlling individual devices of the apparatus containing several devices in such a way that a means for sending an identification signal individualizing the user interface (1) itself and/or the type of the user interface is arranged to each of them. Further, as for part of the user interface (1), a means may be arranged thereto for transmitting the identification signal of the person using the user interface (1) received from a device, from an identification card or equivalent sending the identification signal to the device (2, 3) belonging to the apparatus.

The apparatus according to the invention may thus contain several devices (2, 3) used in the dental care environment connected to a network, such as a dental unit, a patient chair, an intra oral x-ray device, a panoramic x-ray device, a skull imaging x-ray device or a computer tomography device specially designed for imaging the skull area. The operation mode of the user interface (1) may be arranged selectable between several devices, whereupon the control signals may be arranged to be interpret e.g. as signals for controlling a software used by or via a computer, or for controlling a dental unit. Naturally, each device of the apparatus belonging to the dental care environment may also be arranged to be controlled via its traditional control means, too.

According to one preferable embodiment of the invention, at least a portion of the surface of the user interface (1) contains a capacitive or a resistive contact surface. So, according to one preferable embodiment of the invention, the user interface (1) has been arranged to create control information as a response to pressing or sliding on the contact surface and thus causing a change in the capacitance or the resistance dependent on the point of contact. The user interface (1) may be arranged to be used either as a touch pad controlling a cursor only or such that when controlling some device (2, 3), it operates as a touch pad controlling the cursor and when controlling some other device (2, 3), as a touch screen containing a touch pad. The surface of this kind of a user interface (1) may be made of transparent material and be arranged in a manner described above over a display (11) showing selectable control functions. On the surface of the user interface (1), also push buttons or touch keys may be arranged via which the control signals may be transmitted. Further, according to one embodiment of the invention, the surface of the user interface (1) may be arranged to contain sub-areas containing at least two different control technologies.

The invention allows implementing the control arrangement of the computer or other device used in the dental care environment as easily cleanable and disinfectable between dental care operations or imagings, or even during some operations, and especially such that the computer can be used without moving to a working place arranged singly for the use of it. This way, use of the computer in connection with dental care work is remarkably simpler and more hygienic than in many of the prior art solutions. When the computer can be used also with protective gloves, it facilitates controlling of the computer in connection with dental care operations. Placing the user interface in the dental care environment is free and it can be placed in an ergonomically preferable location from the point of view of the dental care work.

Thus, according to the invention, the apparatus located in the dental care environment includes at least one user interface, and control commands are sent according to it to at least one device used in connection with the dental care work, like to a dental unit, to a patient chair, to a dental x-ray device and/or to a computer in such a way that for controlling said at least one device such a user interface is used, whereto a fixed or a detachable means has been arranged for detachably connecting the user interface to a person working in the dental care environment, to his/her clothing or to the dental unit, or which has been arranged to be a fixed or a detachable part of clothing or other structure arranged to be separately dressed on the person in question in such a way that said user interface is attached by said means for detachably connecting it to the person working in the dental care environment, to the person's clothing or to the dental unit, or it is dressed on and control commands are given by it to at least one of said devices. Preferably, the method is used particularly for controlling the dental unit and/or the computer by attaching the user interface to the person's wrist or forearm, for example, whereby the control commands may be given e.g. while holding the dental instrument in hand and without moving away from the care work station.

So, in a method according to one embodiment of the invention, prior to giving control commands to at least one device included in the apparatus, one takes an instrument from an instrument table of a dental unit in hand, initialization the use of which the dental unit has been arranged to recognize, checks from the display arranged to the user interface or elsewhere in the apparatus that the recognition has taken place and gives at least one control command meant for the instrument in question from the user interface. Such a method may contain, instead of the automatic recognition of the instrument, changing of the operation mode of the user interface to concern the desired instrument by a control command given from the user interface. On the other hand, the operation mode of the user interface may be changed by a corresponding control command push button from a dental unit mode to a computer control mode, after which also control commands meant for controlling the computer may be given from the user interface.

A computer included in the apparatus according to one preferable embodiment of the invention can be arranged to be controlled both with the help of a user interface according to the invention and by traditional computer control means according to prior art. Implementing of the invention does not prevent e.g. arranging controlling of the dental unit as well according to prior art, either. The display of the computer possibly belonging to the apparatus may be placed in a suitable location in the dental care environment, such as e.g. by physically attaching it to the dental unit itself. Arrangement according to the invention may be implemented by two displays, i.e. for example in such a way that both the computer and the user interface have their own displays. If desired, one may arrange to be possible to use the display of the computer for presenting information received from e.g. the dental unit, too. Control information may be arranged to be input from the user interface to the computer e.g. via a mouse connection already existing in the computer, or it may be received via some other data transmission arrangement and a driver software arranged to the computer, which software then emulates a mouse towards the computer.

It is obvious to a man skilled in the art that the invention and its embodiments are not limited to the examples described above but e.g. as technique advances, the inventive concept defined in the claims below can be implemented in other ways besides those described above as well.

The invention claimed is:

1. An apparatus in a dental care environment, which apparatus includes at least one device adapted for use in dental care work in a dental care environment, said device selected from the group consisting of a dental unit, a patient chair, a dental x-ray device and a computer, and at least one user interface remote from the at least one device and adapted to send control commands to at least one of said devices used in connection with dental care work, wherein at least one of a fixed and a detachable means is arranged to said user interface to detachably connect the user interface to a person working in the dental care environment, to clothing of the person or to the dental unit, or said user interface is arranged as a fixed or a detachable part of clothing or a structure arranged to be dressed on a person or of some other structure to be dressed on the person and wherein, either,
   i) the user interface comprises a means containing an identification code and a means for sending a signal including the identification code to the at least one device, which code individualizes the user interface or a type of the user interface, or
   ii) the user interface comprises a means to receive and forward a signal including an identification code from or to the at least one device, which signal has been arranged to be received from a device or an identification card carried along by a user of the user interface and sending an identification signal, and further wherein
   the apparatus contains at least two devices which are arranged in functional connection with said user interface in such a way that each of the devices provides an identification signal of substantially equal intensity, and wherein the user interface contains means to recognize, which of the identification signals received from the devices is the strongest, and means for locking the user interface to control the device sending the strongest signal, or wherein the apparatus includes means based on a GPS-technique for locating the location of the user interface with respect to at least two devices included in the apparatus.

2. The apparatus according to claim 1, wherein the apparatus contains at least one display functionally connected to at least one of said devices.

3. The apparatus according to claim 1, wherein the apparatus contains a display of said user interface.

4. The apparatus according to claim 1, wherein at least one display is functionally associated with the at least one of the devices and the user interface, and wherein at least one of said devices contains a means to produce graphics, and the apparatus has a means to transmit graphics to said at least one display.

5. The apparatus according to claim 1, wherein the user interface contains a means to at least send information wirelessly.

6. The apparatus according to claim 1, wherein the user interface further comprises:
   a component capable of storing energy; and
   means to receive energy supplied by an energy source external to the component and the user interface, and to forward the energy to said component.

7. The apparatus according to claim 1, wherein the user interface includes at least a receiver of an induction link, which has been arranged to at least receive energy supplied by an energy source external to the user interface to thereby supply energy to a component capable of storing energy for use by the user interface, whereby the user interface either additionally includes a separate transmitter of a data link or said receiver of the induction link has been arranged to operate also as a transmitter of the data link.

8. The apparatus according to claim 1, wherein the apparatus contains a wireless bidirectional data link between the user interface and at least one device included in the apparatus.

9. The apparatus according to claim 1, wherein said user interface is hermetically tight so that a cold sterilization of the user interface by wiping or submerging the user interface in a sterilization liquid is possible or said user interface is incorporated with a structure having a surface allowing the user interface to endure autoclave sterilization.

10. The apparatus according to claim 1, wherein said user interface includes a touch pad or a touch screen containing a display arranged in connection with said user interface.

11. The apparatus according to claim 1, wherein the user interface has functionalities corresponding mouse functions, including at least either a left click and a right click and a scrolling functionality.

12. The apparatus according to claim 1, further comprising means arranged to said user interface to receive and recognize an identification signal sent by a transmitter arranged in at least one of said devices.

13. The apparatus according to claim 1, wherein the apparatus contains at least two devices used in connection with dental care work and a means arranged to the user interface to change an operation mode of the user interface between controlling at least a first and a second device.

14. The apparatus according to claim 1, wherein the apparatus contains at least two devices connected to a network selected from the group consisting of a dental unit, a patient chair, an intraoral x-ray device, a panoramic x-ray device, a panoramic and skull x-ray imaging device, and a computer tomography imaging device of the skull area.

15. The apparatus according to claim 1, further comprising a detachably connectable part arranged to the user interface, through which said detectably connectable part giving control commands of the user interface has been arranged to take place and which part is such by its structure or by its material that said user interface is autoclavable or otherwise thermally sterilizable.

16. The apparatus according to claim 1, wherein said means for detachably connecting the user interface has a structure allowing the user interface to be attached to at least one of a person's thigh, wrist, forearm and chest.

17. The apparatus according to claim 1, wherein said means for detachably connecting the user interface contains at least one belt or tape for attaching the user interface to a person's wrist.

18. The apparatus according to claim 1, wherein said means for detachably connecting the user interface contains at least one magnetic part.

19. The apparatus according to claim 1, wherein the user interface comprises a position detector operable to recognize the position of the user interface and the user interface comprises a means to change the operating response of a touch pad included in the user interface as a response to recognizing at least one previously determined position of the user interface.

20. The apparatus according to claim 1, wherein said user interface has been arranged to supply commands to software used in connection with dental care, wherein the software executes commands on at least one of said devices.

21. The apparatus according to claim 1, wherein said at least one device is a computer used in connection with dental care work, said computer containing a database into which at least one software application used in connection with dental care work is stored, which computer has been arranged in functional connection with at least one display for controlling said at least one software application from said user interface on said display.

22. An apparatus in a dental care environment, which apparatus includes at least one device adapted for use in dental care work in a dental care environment, said device selected from the group consisting of a dental unit, a patient chair, a dental x-ray device and a computer, and at least one user interface remote from the at least one device and adapted to send control commands to at least one of said devices used in connection with dental care work, wherein at least one of a fixed and a detachable means is arranged to said user interface to detachably connect the user interface to a person working in the dental care environment, to clothing of the person or to the dental unit, or said user interface is arranged as a fixed or a detachable part of clothing or a structure arranged to be dressed on a person or of some other structure to be dressed on the person, wherein the apparatus contains at least two devices which are arranged in functional connection with said user interface in such a way that each of the devices provides an identification signal of substantially equal intensity, and wherein the user interface contains means to recognize, which of the identification signals received from the devices is the strongest, and means for locking the user interface to control the device sending the strongest signal, or wherein the apparatus includes corresponding means based on a GPS-technique, for locating the location of the user interface with respect to at least two devices included in the apparatus.

23. The apparatus according to claim 22, wherein the user interface includes at least a receiver of an induction link, which has been arranged to at least receive energy supplied by an energy source external to the user interface to thereby supply energy to a component capable of storing energy for use by the user interface, whereby the user interface either additionally includes a separate transmitter of a data link or said receiver of the induction link has been arranged to operate also as a transmitter of the data link.

24. The apparatus according to claim 22, wherein the apparatus contains a wireless bidirectional data link between the user interface and at least one device included in the apparatus.

25. The apparatus according to claim 22, wherein said user interface is hermetically tight so that a cold sterilization of the user interface by wiping or submerging the user interface in a sterilization liquid is possible or said user interface is incorporated with a structure having a surface allowing the user interface to endure autoclave sterilization.

26. The apparatus according to claim 22, wherein the apparatus contains at least two devices used in connection with dental care work and a means arranged to the user interface to change an operation mode of the user interface between controlling at least a first and a second device.

27. The apparatus according to claim 22, wherein the apparatus contains at least two devices connected to a network selected from the group consisting of a dental unit, a patient chair, an intraoral x-ray device, a panoramic x-ray device, a panoramic and skull x-ray imaging device, and a computer tomography imaging device of the skull area.

28. The apparatus according to claim 22, further comprising a detachably connectable part arranged to the user interface, through which said detectably connectable part giving control commands of the user interface has been arranged to take place and which part is such by its structure or by its material that said user interface is autoclavable or otherwise thermally sterilizable.

29. The apparatus according to claim 22, wherein said means for detachably connecting the user interface has a structure allowing the user interface to be attached to at least one of a person's thigh, wrist, forearm and chest.

30. The apparatus according to claim 22, wherein said user interface has been arranged to supply commands to software used in connection with dental care, wherein the software executes commands on at least one of said devices.

31. The apparatus according to claim 22, wherein said at least one device is a computer used in connection with dental care work, said computer containing a database into which at least one software application used in connection with dental care work is stored, which computer has been arranged in functional connection with at least one display for controlling said at least one software application from said user interface on said display.

32. A method for controlling at least one device selected from the group consisting of a dental unit, a patient chair, a dental x-ray device and a computer, said at least one device being disposed in an apparatus located in dental care environment and used in connection with dental care work, which apparatus includes at least one user interface remote from the at least one device and adapted to send control commands to at least one of said devices used in connection with dental care work, said method comprising:
 controlling said at least one device by using the user interface, said user interface:
 (1) being incorporated with a fixed or a detachable means forming a detachable connection of the user interface to a person working in the dental care environment or to clothing of a person, or
 (2) being arranged on a fixed or a detachable part of clothing or another structure arranged to be dressed on a person in such a way that said user interface is attached by said means for detachably connecting said user interface to a person working in the dental care environment, or to a person's clothing;
 the controlling including dressing said user interface on a person, and giving at least one control command by said user interface to at least one of said devices, wherein, prior to giving said at least one control command to said at least one device, a user of the user interface takes an instrument from an instrument table of the dental unit in hand, which operation the dental unit recognizes, and gives at least one control command from the user interface to said instrument.

33. The method according to claim 32, wherein at least one of a dental unit and the computer is controlled by said user interface.

34. The method according to claim 32, wherein said user interface is attached to said person's wrist or forearm.

35. A method for controlling at least one device selected from the group consisting of a dental unit, a patient chair, a dental x-ray device and a computer, said at least one device being disposed in an apparatus located in dental care environment and used in connection with dental care work, which apparatus includes at least one user interface remote from the at least one device and adapted to send control commands to at least one of said devices used in connection with dental care work, said method comprising:

controlling said at least one device by using the user interface, said user interface:
(1) being incorporated with a fixed or a detachable means forming a detachable connection of the user interface to a person working in the dental care environment or to clothing of a person, or
(2) being arranged on a fixed or a detachable part of clothing or another structure arranged to be dressed on a person in such a way that said user interface is attached by said means for detachably connecting said user interface to a person working in the dental care environment, or to a person's clothing;
the controlling including dressing said user interface on a person, and giving at least one control command by said user interface to at least one of said devices, wherein, prior to giving said at least one control command to said at least one device, a user of the user interface takes an instrument from an instrument table of the dental unit in hand, and while keeping the instrument in hand changes, in case needed, the operation mode of said user interface to a computer controlling mode by a control command giving means arranged in the user interface and gives at least one control command for controlling a computer from said user interface.

36. The method according to claim 35, wherein at least one of a dental unit and the computer is controlled by said user interface.

37. The method according to claim 35, wherein said user interface is attached to said person's wrist or forearm.

* * * * *